United States Patent [19]

Tietze

[11] Patent Number: 5,573,154
[45] Date of Patent: Nov. 12, 1996

[54] BACKPACK FOR HOLDING IMPLEMENTS FOR EMERGENCY MEDICAL CARE

[75] Inventor: Bernd Tietze, Gelnhausen, Germany

[73] Assignee: Heraeus Med GmbH, Hanau, Germany

[21] Appl. No.: 390,847

[22] Filed: Feb. 17, 1995

[30] Foreign Application Priority Data

Feb. 24, 1994 [DE] Germany ............... 44 05 951.5

[51] Int. Cl.⁶ ............................................. A45F 4/02
[52] U.S. Cl. .................. 224/153; 224/582; 224/586; 224/651; 224/652; 224/901.8; 190/110
[58] Field of Search ................... 224/153, 582, 224/586, 651, 652, 650, 655, 627, 901.2, 901.8, 151, 209, 214, 901, 904, 211; 190/110, 114, 109, 111; 206/363, 370, 438, 570, 828, 803; 383/4, 38, 39, 40

[56] References Cited

U.S. PATENT DOCUMENTS

| 116,874 | 7/1871 | Schaefer | 224/209 |
|---|---|---|---|
| 1,217,357 | 2/1917 | Sparrow | 383/39 |
| 2,704,077 | 3/1955 | Prillaman | 402/4 |
| 4,169,550 | 10/1979 | Williams | 224/211 |
| 4,386,642 | 6/1983 | Durbin | 190/110 |
| 4,515,493 | 5/1985 | Radovich | 383/4 |
| 4,796,790 | 1/1989 | Hamilton | 206/803 |
| 4,874,119 | 10/1989 | Winter | 190/110 |
| 4,973,177 | 11/1990 | Rose | 24/10 R |
| 4,993,614 | 2/1991 | Bonofiglo | 224/904 |
| 5,020,711 | 6/1991 | Kelley | 224/901 |
| 5,152,441 | 10/1992 | Torena | 224/209 |
| 5,215,398 | 6/1993 | White et al. | 402/70 |
| 5,350,249 | 9/1994 | Peters | 402/4 |

FOREIGN PATENT DOCUMENTS

| 167038 | 4/1950 | Austria | 224/209 |
|---|---|---|---|
| 0 199 853 A1 | 11/1986 | European Pat. Off. . | |
| 89170 | 3/1870 | France | 224/209 |
| 2577771 | 8/1986 | France | 190/110 |
| 2 626 166-A1 | 7/1989 | France . | |
| 303540 | 2/1918 | Germany | 224/156 |
| 308222 | 10/1918 | Germany | 224/209 |
| 623012 | 12/1935 | Germany | 224/209 |
| 2907164 | 8/1979 | Germany | 224/153 |
| 9316657 U | 8/1994 | Germany . | |
| 117 | 1/1860 | United Kingdom | 224/209 |
| 29532 | 11/1913 | United Kingdom . | |
| WO93/21793 | 11/1993 | WIPO . | |

OTHER PUBLICATIONS

Patent #361,688 to Robert in class 224, Subclass 209; Sep. 29, 1906; Country unknown.
Exworld Brochure–Thomas's Advance Life Support Pack.

Primary Examiner—Henry J. Recla
Assistant Examiner—Gregory M. Vidovich
Attorney, Agent, or Firm—Panitch Schwarze Jacobs & Nadel, P.C.

[57] ABSTRACT

A backpack for holding implements for emergency medical care, includes an approximately rectangular rear wall part and a front wall part which swings open, is joined with the rear wall part by means of a first side wall part, and corresponds approximately to the rear wall part in terms of its surface area. The backpack also includes a carrying system. In order to create a backpack of this type, which ensures the visibility of its entire contents at first glance and from which the implements for emergency medical care can be easily removed by the user without it first being necessary for other components of the backpack's contents to be removed, a second side wall part, which is joined with an intermediate wall part that can swing open, is arranged on the rear wall part opposite the first side wall part. In addition, two end flaps are arranged at the free sides of the rear wall part. These are opposite each other and, when the backpack is closed, they at least partially surround the side wall parts. At least the rear wall part, the intermediate wall part and the front wall part include means for securing or holding the implements for emergency medical care.

7 Claims, 1 Drawing Sheet

BACKPACK FOR HOLDING IMPLEMENTS FOR EMERGENCY MEDICAL CARE

FIELD OF THE INVENTION

The invention pertains to a backpack for holding implements for emergency medical care, with an approximately rectangular rear wall part and with a front wall part which swings open and is joined with the rear wall part by means of a first side wall part and which corresponds approximately to the rear wall part in terms of its surface area, and that has a carrying system.

BACKGROUND OF THE INVENTION

A backpack of such a type is known, for example, as the "Thomas Emergency Medical Pack." This backpack is designed in the shape of a suitcase with a lower part and with a cover that swings open. Carrying straps are arranged on the lower part. Pockets for holding implements are attached to the lower part and the cover. The interior of the backpack holds various implements for emergency medical care, which are arranged in the interior in a fitted fashion. This backpack does not, however, ensure maximum visibility of the contents, partly because the implements are arranged on top of each other, and partly because it is impossible to see into the corners and the sides of the lower part, so that it is not certain that everything will be seen at first glance. As a result of that, handling is made more difficult, since the user is always required to remove some portion of the contents of the backpack in order to attain access to other implements.

SUMMARY OF THE INVENTION

The invention therefore has as an object the creation of a backpack of the type described at the outset, but which guarantees the visibility of its entire contents at first glance and from which the implements for emergency medical care can be easily removed by the user without it first being necessary for other components of the backpack's contents to be removed. This object is achieved in accordance with the invention by providing on the rear wall part, opposite the first side wall part, a second side wall part, which is joined with an intermediate wall part that can swing open. At the free ends of the rear wall part two end parts are arranged opposite each other, which at least partially surround the side wall parts and the front wall part when the backpack is closed. At least the rear wall part, the intermediate wall part and the front wall part have means for securing or holding the implements for emergency medical care.

Such an arrangement guarantees that the backpack can be swung open to form a single flat surface on which the implements for emergency medical care are arranged along side each other in a clearly visible fashion. The organization of this flat surface makes it possible to arrange the implements in groups according to their specialized purposes, so that the user is immediately given a clear overview and is able to identify in which part of the backpack the implements that are needed at that moment are located, so that he only needs to concentrate on the implement group he needs, and can allow the other parts of the backpack surfaces and their implements to go unheeded without first having to remove them and put them aside. Faster and more certain access to the specific materials is thereby assured, and the danger of confusing different implements is practically eliminated.

It is helpful if the side wall parts and/or the end parts also include means for securing or holding implements for emergency medical care. As a result of that, the entire available surface area can be used. Advantageously, the means for securing are configured as adhesive surfaces (so-called hook-and-loop (e.g. Velcro) closures) or as holding straps. Such securing means ensure simple and rapid removal of the individual implements. It is possible to group the individual implements in different ways (according to purpose, for example), or to exchange individual implements for other ones, so that the same securing means may hold a variety of implements. Providing the end flaps with pockets is helpful in creating additional room for smaller objects, for instance, which cannot be retained on adhesive surfaces or by means of holding straps.

It is also advantageous if the means for holding the implements for emergency medical care are configured as pockets. These pockets can be made of a transparent material and, just as the pockets of the end flaps, can be used for holding parts that are smaller or otherwise difficult to secure. It is also possible for the pockets to be placed in a removable fashion on adhesive wall surfaces, in order to ensure the rapid exchange of pockets or an arrangement that corresponds to the intended purpose. The pockets of the backpack can be standardized in a beneficial fashion, that is, the size and the design are selected in such a way that the pockets can also be inserted into other transport containers. It is thereby possible to satisfy different uses in emergency medical care with a series of matching transport containers. In addition, this universal interchangeability of the pockets also ensures their flexible arrangement within the backpack, in order to allow for the optimum selection for a variety of uses. Also, with such a standardized implementation or configuration of the pockets, a simpler and less expensive provision of replacement parts or items that are subject to wear is possible.

Brief Description of the Drawing

The foregoing summary, as well as the following detailed description of a preferred embodiment of the invention, will be better understood when read in conjunction with the appended drawing which show further features and advantages of the invention. For the purpose of illustrating the invention, there is shown in the drawing an embodiment which is presently preferred. It should be understood, however, that the invention is not limited to the precise arrangements and instrumentalities shown. In the drawing.

DETAILED DESCRIPTION OF PREFERRED EMBODIMENT

Figure 1:
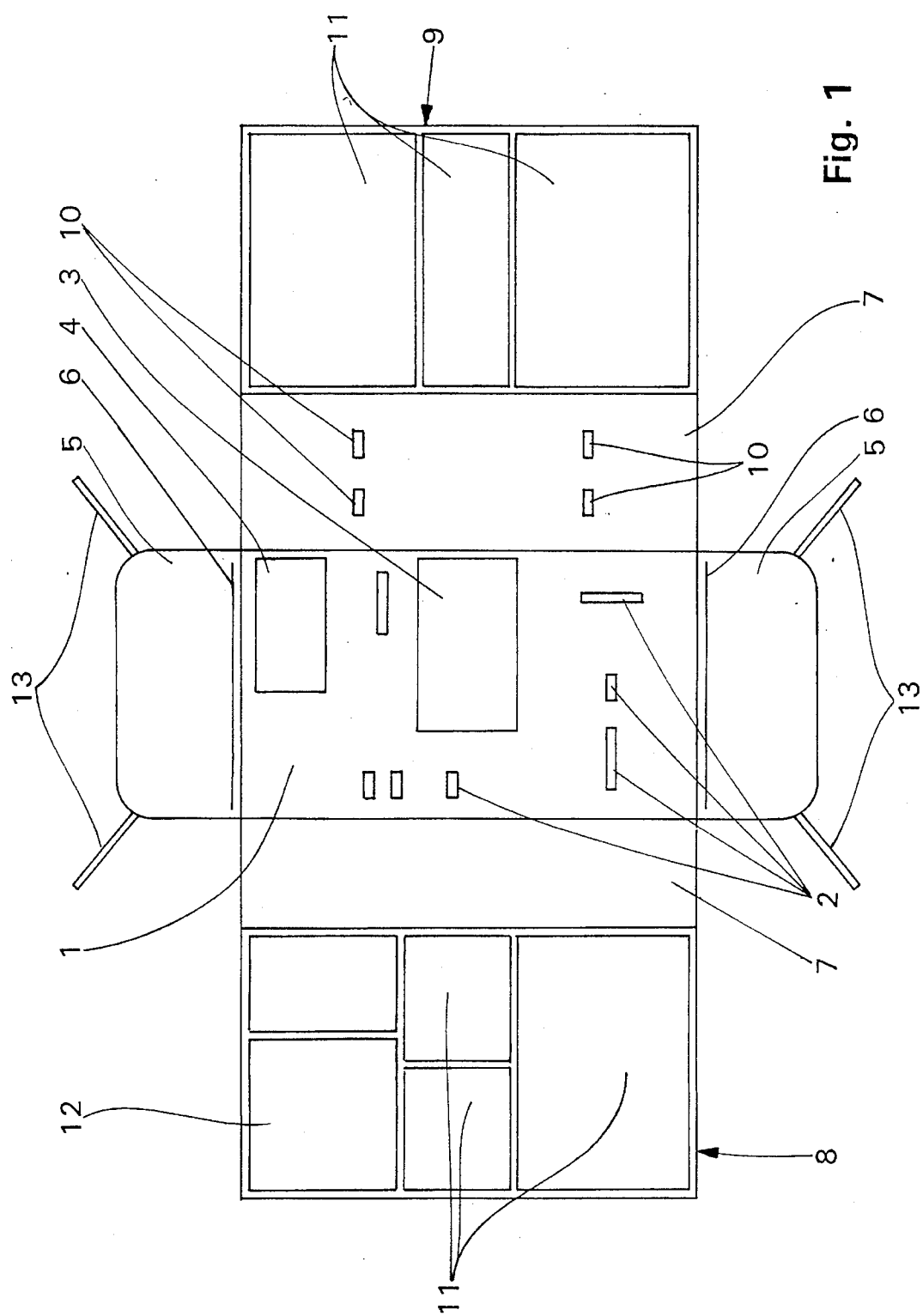
FIG. 1 shows in plan view an emergency backpack in accordance with the invention, completely opened. All directions (e.g., left, right, upper, lower) used below refer to the orientation of the drawing and do not necessarily correspond to the orientation of the backpack in use.

As its central part, the backpack features the rear wall part 1. A conventional, preferably high-quality carrying framework (not shown), of the type that is known for backpacks, is arranged on the reverse side of the rear wall part 1. On its front side (facing the viewer), which is facing the interior of the backpack, the rear wall part 1 features numerous adhesive surfaces 2, to which pockets or other implements of emergency medical care can be secured. In addition, an oxygen respirator 3 and a suction pump 4 are arranged on the rear wall part 1. The placement of the suction pump 4 and the oxygen respirator 3 is carried out on the rear wall part 1, because these relatively heavy pieces of equipment can be most securely attached there and thus ensure the best carrying comfort.

Arranged on the upper and lower sides of the rear wall part 1 are end flaps 5, that have pockets which can be closed with zipper closures 6. Arranged to the left and the right of the rear wall part 1 are side wall parts 7, to one of which the intermediate (partition) wall part 8 is joined, and to the other of which the front wall part 9 is joined. Arranged on the side wall part 7 that joins the rear wall part 1 and the front wall part 9, are holding straps 10, with which longer objects such as splints, for example, can be secured in the backpack.

Pockets 11 are attached to the intermediate wall part 8 and the front wall part 9 by means of adhesive surfaces that in the drawing are covered by the pockets 11. These pockets contain, for example, bandaging materials, equipment for emergency intubation, or other implements. In addition, an ampule case 12 is arranged on the intermediate wall part 8. The ampule case 12 and the pockets 11 are preferably made of a transparent material so that the contents can be recognized immediately.

An arrangement of this type makes it possible almost at will to re-group the implements within the backpack for emergency medical care, and the pockets can be outfitted depending on the intended purpose and grouped in an appropriate fashion, so that the backpack can, for example, be spread out among a group of injured persons in such a way that the appropriate implements are located in the immediate vicinity of each injured person. The implements can also be removed easily, with no possibility of confusion, and be used for emergency care.

The backpack is closed by first folding the intermediate wall part 8 over the rear wall part 1, and then laying the front wall part 9 over the intermediate wall part 8. Following that, the two end parts 5 are drawn over the corresponding ends of the wall parts. The flaps or end parts (5) at least partially cover or overlap the side wall parts (7). The closure of the backpack is carried out additionally by means of the closing straps 13, which may be tied together or fastened to the outside of the front wall part by snaps or Velcro, for example.

It will be appreciated by those skilled in the art that changes could be made to the embodiment described above without departing from the broad inventive concept thereof.

It is understood, therefore, that this invention is not limited to the particular embodiment disclosed, but it is intended to cover modifications within the spirit and scope of the present invention as defined by the appended claims.

I claim:

1. Backpack for holding implements for emergency medical care comprising an approximately rectangular rear wall part, a front wall part that swings open and that is joined with the rear wall part by means of a first side wall part, the front wall part corresponding approximately to the rear wall part in terms of its surface area, a second side wall part arranged on the rear wall part opposite the first side wall part, an intermediate wall part which is joined to said second wall part and is adapted to swing open, two end flaps arranged opposite each other at free sides of the rear wall part, the backpack being adapted to be moved from a first, closed configuration to a second, open configuration, with the front, intermediate, side and rear wall parts and the flaps forming a single flat surface in the open configuration, and the flaps at least partially overlap the side wall parts and the front wall part when the backpack is closed, and implements for emergency medical care, said implements being secured to at least the rear wall part, the intermediate wall part and the front wall part by means for securing the implements for emergency medical care.

2. The backpack according to claim 1, wherein at least one of the two side wall parts and the two end flaps has means for securing the implements for emergency medical care.

3. The backpack according to claim 1, wherein the means for securing comprise adhesive surfaces.

4. The backpack according to claim 1, wherein at least one of said side wall parts includes the means for securing implements for emergency medical care comprising holding straps.

5. The backpack according to claim 1, wherein the end flaps have pockets.

6. The backpack according to claim 1, wherein the means for securing the implements for emergency medical care at least comprise pockets.

7. The backpack according to claim 1, wherein said means for securing the implements at least comprise pockets removably arranged on adhesive areas on said backpack.

* * * * *